United States Patent [19]

Graham et al.

[11] Patent Number: 5,234,410
[45] Date of Patent: Aug. 10, 1993

[54] CATHETER ASSEMBLY

[75] Inventors: Chad D. Graham, Bell Buckle, Tenn.; Rex R. Weeks, Rapid City, S. Dak.

[73] Assignee: VLV Associates, East Hanover, N.J.

[21] Appl. No.: 965,339

[22] Filed: Oct. 23, 1992

[51] Int. Cl.⁵ .............................................. A61M 25/00
[52] U.S. Cl. .................................... 604/167; 604/256; 251/149.1
[58] Field of Search ............... 604/167, 168, 164, 256, 604/169, 264; 251/149.1

[56] References Cited

U.S. PATENT DOCUMENTS

| | | | |
|---|---|---|---|
| 4,430,081 | 2/1984 | Timmermans | 251/149.1 |
| 4,874,377 | 10/1989 | Newgard et al. | 604/167 |
| 5,009,391 | 4/1991 | Steigerwald | 604/167 |
| 5,064,416 | 11/1991 | Newgard et al. | 604/167 |
| 5,084,023 | 1/1992 | Lemieux | 604/167 |
| 5,085,645 | 2/1992 | Purdy et al. | 604/167 |
| 5,092,846 | 3/1992 | Nishijima et al. | 604/167 |
| 5,092,857 | 3/1992 | Fleischhacker | 604/167 |

*Primary Examiner*—John G. Weiss
*Attorney, Agent, or Firm*—Kenyon & Kenyon

[57] ABSTRACT

The catheter assembly is provided with a conventional catheter which extends from a hub. In addition, a tube or blunt needle is mounted within the hub coaxially of the catheter and is provided with an elastomeric valve over the open end. The elastomeric valve is formed by a pair of rubber sheaths, each of which has a closed end for sealing the tube against a back flow of blood. The sheaths can be pierced by a needle in order to perform a venipuncture while re-sealing upon removal of the needle. The catheter assembly may also be connected with a male luer connector in a manner to push the sheaths over the tube so as to expose the lumen of the catheter to the connector.

14 Claims, 1 Drawing Sheet

CATHETER ASSEMBLY

This invention relates to a catheter assembly. More particularly, this invention relates to an intravenous catheter assembly.

Heretofore, various types of catheters and catheter assemblies have been known for insertion in a vein of a patient. One of the most popular intravenous (IV) catheters in use is known as the over-the-needle catheter. In this case, the catheter is constructed of a hub from which a catheter needle extends. This catheter is constructed so as to receive a needle assembly having a needle which passes into and through the catheter needle. In use, the needle of the needle assembly is first inserted into the vein of a patient and, thereafter, the catheter is pushed over this needle into the vein. At the same time, in some cases, the needle of the needle assembly is simultaneously removed from the vein so as to leave the catheter needle in place.

Generally, such a catheter assembly has required the connection of a pre-primed IV administration set to the catheter hub in order to preclude a back flow of blood from the vein of the patient through the hub to the surrounding environment. Consequently, one of the major disadvantages of such a catheter is the requirement for manipulation of the administration set and/or manual dexterity in utilizing the catheter assembly.

Another disadvantage of the catheter assembly of the above type is that a significant percentage of the incidence of sepsis may be directly attributable to the manipulation of the administration set with the catheter assembly during a venipuncture procedure. Still another disadvantage is that there may be an escape of blood into the surrounding environment.

Accordingly, it is an object of the invention to be able to perform a bloodless venipuncture using a catheter assembly.

It is another object of the invention to provide an improved IV catheter assembly in which blood is contained within a catheter after implantation in a vein.

It is another object of the invention to be able to hook up a conventional male luer fitting to a catheter hub and obtain fluid flow without undue pressure drop.

It is another object of the invention to be able to hook up a syringe directly to a catheter hub to obtain a blood sample without having to use a needle.

Briefly, the invention provides a catheter assembly which is comprised of a hub, a catheter secured to and extending from the hub to define a flow path, a tube secured to and within the hub to define a flow path with the tube being coaxial with the catheter and an elastomeric valve mounted on one end of the tube remote from the catheter and within the hub. In addition, the valve has a pair of walls disposed in spaced apart relation transversely of the tube in order to seal the end of the tube against a flow of blood from the catheter needle.

The elastomeric valve for sealing over the end of the tube may be constructed of a pair of sheaths which are disposed over the tube in overlying relation. In this case, each sheath has a closed end which defines a respective one of the walls for sealing over the end of the tube. Each sheath may be made, for example, of rubber or any other suitable material. In addition, each sheath is constructed so that the wall has a thickness in the range of from 0.010 inch to 0.040 inch.

In one embodiment, the catheter assembly is combined with a needle assembly having a needle piercing the elastomeric walls of the valves. In this embodiment, the needle of the needle assembly is disposed coaxially within the tube and the catheter of the catheter assembly for passage into a vein as is known.

In this latter embodiment, the needle of the needle assembly is utilized in a conventional manner so as to puncture a vein in a patient. Thereafter, the catheter can be slid down over the needle of the needle assembly into the patient's vein. At the same time or shortly thereafter, the needle assembly is withdrawn from the catheter assembly so as to withdraw the needle of the needle assembly from the patient's vein as well as from the catheter assembly. Upon withdrawal of the needle assembly, the two pierced elastomeric walls of the elastomeric valve tend to close thereby shutting off the flow of blood into the catheter hub. Blood thus ceases to flow through the catheter until a further connector is placed over the catheter hub. For example, the blunt front end of a luer connector, for example, made in accordance with recognized medical industry ANSI (American National Standards Institute) specifications to which most connectors used in IV therapy must adhere, moves forward and pushes the two elastomeric walls back over the tube within the catheter hub thereby exposing the interior lumen of the tube for purposes of fluid flow between the vein of the patient and, for example, an IV administration set.

During the above procedure, the catheter assembly may be opened to inject fluids. For example, after the needle assembly has been removed from the catheter assembly, a syringe or secondary line set can be connected to the catheter assembly without blood exiting from the patient and potentially contaminating a bed sheet or practitioner.

The construction of the catheter assembly is based on the discovery that when two membranes are interposed within the path of the fluid lumen and pierced, there is no blood flow upon removal of the piercing needle. This has not been found to be true when only one membrane is used.

Also, it does not appear to be necessary to bias a rubber membrane so that there is an external force exerted on the membrane tending to close the pierced wall. Instead, the elasticity of the rubber material appears to be sufficient to lower the size of the opening caused by the needle assembly sufficiently that when two membranes are mounted in series, the resultant valve will shut off blood flow.

A major advantage of the catheter construction is that the walls of the elastomeric valve may be very thin, for example, of a thickness in the range of from 0.010 inches to 0.040 inches. As a result, since no external biasing force is required, the force necessary to remove the needle of the needle assembly after venipuncture is accomplished, or alternatively, the force required to push off the catheter assembly from the needle, is very low (for example, in the gram range) thereby preserving a major attribute of the existing over-the-needle venipuncture insertion technique. In this respect, nurses and other practitioners generally desire the force to push the catheter assembly off the needle to be as small as possible thereby being able to "feel" the catheter going through the skin and into the vein of the patient.

These and other objects and advantages of the invention will become more apparent from the following detailed description taken in conjunction with the accompanying drawings wherein.

Figure 1:
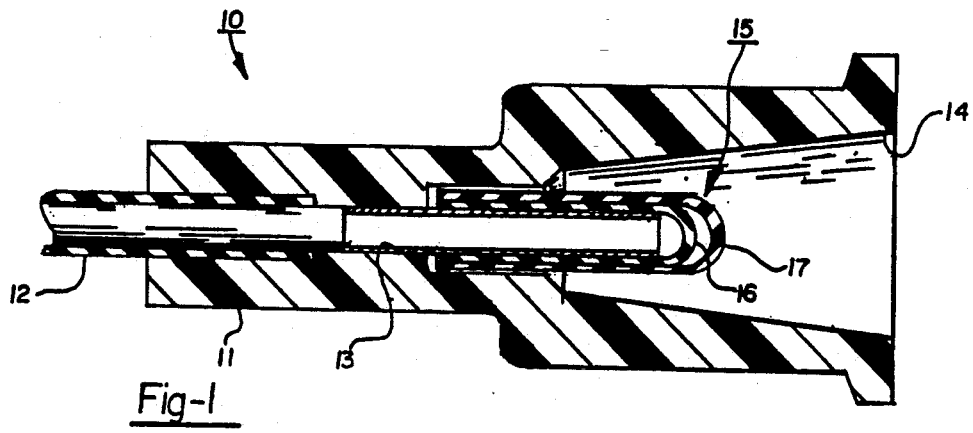
FIG. 1 illustrates a cross sectional view of a catheter assembly constructed in accordance invention.

Referring to FIG. 1, the catheter assembly 10 includes a hub 11 of conventional structure, a catheter 12 which is secured to and which extends from the hub 11 to define a flow path and a tube 13 which is secured to and within the hub 11 coaxially of the catheter 12 in order to define a coaxial flow path.

As illustrated, the hub 11 which may be made of a plastic material has a conically shaped bore 14 at one end and is generally thin-walled about the bore 14.

As indicated, the tube 13 which may be in the form of a stainless steel needle is sealed within the hub 11, for example, using adhesive, an interference fit or other suitable connection means. The tube 13 extends within the bore 14 of the hub 11 and terminates at a point spaced within the interior of the hub 11.

As indicated in FIG. 1, the tube 13 has an internal diameter which is less than the internal diameter of lumen of the catheter 12. However, the relative sizes of the lumen for the tube 13 and catheter 12 may be the same or may be greater, as the case may be, depending upon manufacturing techniques.

An elastomeric valve 15 is mounted on the end of the tube 13 remote from the catheter 12 and within the bore 14 of the hub 11. This valve 15 is formed, for example, of a pair of sheaths 16, 17 which are disposed over the tube 13 in overlying relation with each sheath 16, 17 having a closed end defining a wall disposed transversely of the tube 13 in order to seal the end of the tube 13 against a flow of blood from the catheter 12. Each sheath 16, 17 may be made of rubber or any other suitable elastomeric material. In addition, each sheath 16, 17 is made so that the walls which seal over the end of the tube 13 have a thickness in the range from 0.010 inches to 0.040 inches.

As illustrated, the closed ends of the sheaths 16, 17 are disposed in spaced relation to each other to define a gap or chamber therebetween while the interior sheath 16 is spaced from the end of the tube 13. In addition, the sheaths 16, 17 are recessed within the bore 14 of the hub 11. In addition the tube 13 has a tapered end within the sheaths 16, 17 in facing relation to the walls to facilitate passage of the sheaths 16, 17 thereover.

Figure 2:
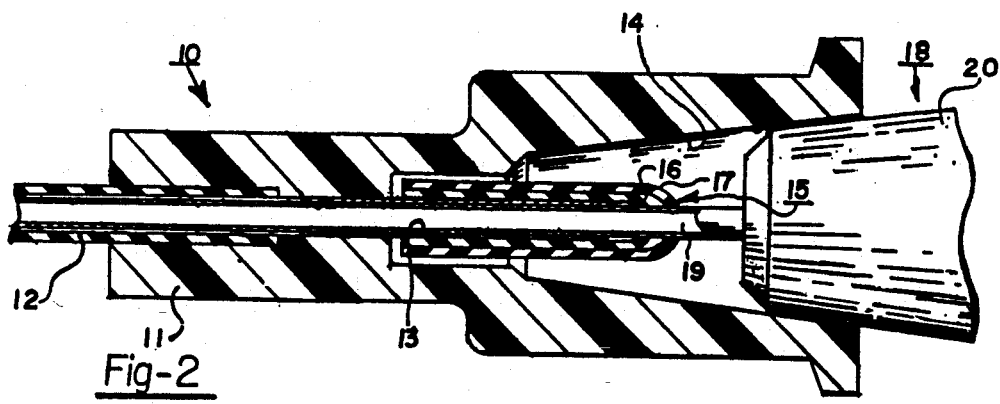
FIG. 2 illustrates a cross sectional view of a catheter assembly connected with a needle assembly in accordance with the invention.

Referring to FIG. 2, wherein like reference characters indicate like parts as above, the catheter assembly 10 is used in combination with a needle assembly 18 in order to carry out a venipuncture. In this respect, the needle assembly 18 has a needle 19 which is mounted in and which projects from a clear plastic needle holder 20. This needle 19 is sized so as to be disposed coaxially within the tube 13 and catheter 12 of the catheter assembly 10 while being of a length to extend from the catheter 12 for passage into a vein of a patient (not shown). In addition, the needle 19 of the needle assembly 18 has a sharp end for piercing through the walls of the two sheaths 16, 17 in seal-tight relation. As illustrated, the closed ends of the sheaths 16, 17 seal over the needle 19 while retaining a closed chamber therebetween.

As indicated in FIG. 2, the needle holder 20 may be sized and shaped so as to be disposed within the bore 14 of the hub 11 of the catheter assembly 10 when the needle 19 of the needle assembly 18 has been inserted into a vein.

In use, the needle 19 of the needle assembly 18 can be passed through the skin of a patient into a vein such as a peripheral vein, using a known technique. Upon venipuncture, blood will flow through the lumen of the needle 19 and into the clear plastic needle holder 20, at which time, blood (flashback) will be seen. This is an indication to the practitioner that the vein has been penetrated and that the procedure may advance to the next stage. Thereafter, the catheter assembly 10 can be pushed over the needle 19 for passage of the catheter 12 into the vein. At the same time or shortly thereafter, the needle assembly needle 19 is withdrawn from the vein as well as from the catheter 10. At this time, the sheaths 16, 17 of the catheter assembly valve 15 return to the position as shown in FIG. 1. That is, withdrawal of the needle 19 allows the openings caused by the needle 19 to close. As such, the two sheaths 16, 17 present two membranes to block any back flow of blood from the catheter 12 and tube 14. Thus, upon removal of the needle assembly 18, there is blood from the patient in the lumen of the catheter needle 12 and the lumen of the tube 13 up to and including the two sheaths 16, 17 but not beyond. The catheter assembly 10 may be left in this condition without concern for blood leakage.

As noted above, it has been found that when two membranes (sheaths) are interposed within the path of the fluid lumen and pierced, upon removal of the piercing needle 19 there is no blood flow passed the membranes. This has not been found to be true when only one membrane is used. Further, it has been found to be unnecessary to bias the elastomeric sheaths 16, 17 so as to provide an external force which tends to close the pierced walls. Instead, the elasticity of the elastomeric material appears to be sufficient to lower the size of the opening sufficiently so that the series arrangement of the two walls of the sheaths 16, 17 are sufficient to close off any blood flow from the tube 13 and needle 12.

As also noted above, a major advantage of the elastomeric valve 15 is that the membranes or walls may be very thin. As a result, and since no external biasing force is required, the force necessary to remove the needle assembly needle 19 after venipuncture is accomplished, or alternately, the force required to push off the catheter 12 from the needle 19, is very low such as in the gram range. This preserves a major attribute of the existing over-the-needle venipuncture insertion technique wherein one may "feel" the catheter 12 passing through the skin and into the vein of the patient.

Figure 3:
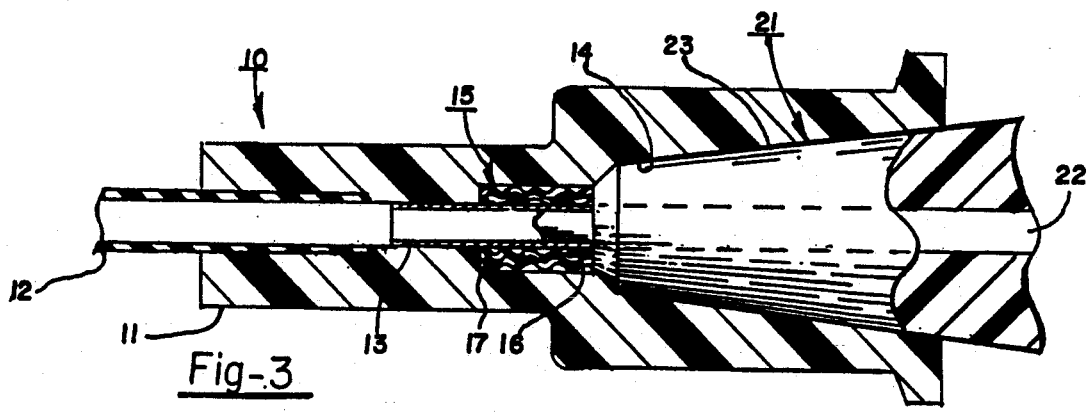
FIG. 3 illustrates a connection between the catheter assembly of FIG. 1 and a male luer hub in accordance with the invention.

Referring to FIG. 3, wherein like reference characters indicate like parts as above, the catheter assembly 10 may also be used in combination with a male luer connector 21. As indicated, the connector 21 has a longitudinal bore 22 which slidably receives one end of the tube 13 of the catheter assembly 10 in seal-tight relation. In addition, a forward end 23 of the connector 21 is matingly received in the bore 14 of the catheter hub 11. As indicated, this forward end 23 serves to push the sheaths 16, 17 over the end of the tube 13 so that the sheaths 16, 17 become compressed between the forward end 23 of the connector 21 and an interior of the hub 11. Upon removal of the connector 21 from the hub 11, the sheaths 16, 17 expand into a position as indicated in FIG. 1 sealing over the end of the tube 13 to seal against a flow of blood from the catheter 12.

The action of the male luer connector 21 in pushing the sheaths 16, 17 of the elastomeric valve 15 over the tube 13 accomplishes two objectives. First, the connector 21 may now be secured in a normal manner to the female luer hub 11 and secondly, the lumen to the catheter 12 is opened allowing for fluid communication between the vein of a patient and a connected administration set (not shown) which is connected with the male luer connector 21. There is no need for a needle to pierce the sheaths 16, 17 to obtain a blood sample.

Of note, in the embodiment illustrated in FIG. 3, a spring means may be provided to assist the return of the compressed sheaths 16, 17 over the tube 13 upon removal of the male luer connector 21.

The invention thus provides a catheter assembly which is able to prevent blood back flow and leakage upon removal of a needle assembly from a catheter of the catheter assembly. In this respect, the catheter may remain in place without need to seal the exposed end of the hub as the two sheaths 16, 17 provide a sufficient seal to prevent leakage of blood. In this sense, the catheter assembly has a self-sealing characteristic. Furthermore, this sealing effect is obtained using relatively thin membranes instead of, for example, a large stopper or the like in the exposed end of the hub of the catheter assembly or some other structure to close off the catheter.

Further, the invention provides a catheter assembly which can be hooked up to a conventional male luer connector to obtain fluid flow without undue pressure drop.

Should the need arise, a syringe may also be directly hooked up to the catheter hub 11 in order to obtain a blood sample without having to use a needle.

What is claimed is:

1. A catheter assembly comprising
   a hub;
   a catheter secured to and extending from said hub to define a flow path;
   a tube secured to and within said hub to define a flow path, said tube being coaxial with said catheter; and
   an elastomeric valve mounted on one end of said tube remote from said catheter and within said hub, said valve having a pair of walls disposed in spaced apart relation transversely of said tube to seal said one end of said tube against a flow of blood from said catheter.

2. A catheter assembly as set forth in claim 1 wherein said elastomeric valve includes a pair of sheaths disposed over said tube in overlying relation, each sheath having a closed end defining a respective one of said walls.

3. A catheter assembly as set forth in claim 2 wherein said sheath is made of rubber.

4. A catheter assembly as set forth in claim 2 wherein each wall has a thickness in the range of from 0.010 inches to 0.040 inch.

5. A catheter assembly as set forth in claim 1 wherein said hub has a conically shaped bore for receiving a tapered male luer hub therein in mating relation.

6. A combination comprising
   a catheter assembly having a hub, a catheter secured to and extending from said hub to define a flow path, a tube secured to and within said hub coaxially of said catheter; and an elastomeric valve on one end of said tube, said valve having a pair of walls disposed transversely of said tube to seal said one end of said tube against a flow of blood from said catheter; and
   a needle assembly having a needle piercing said walls and disposed coaxially within said tube and said catheter, said needle being disposed to extend from said catheter for passage into a vein.

7. The combination as set forth in claim 6 wherein said needle assembly includes a holder mounting said needle therein and being disposed in said hub.

8. The combination as set forth in claim 6 wherein said elastomeric valve includes a pair of sheaths disposed over said tube in overlying relation, each sheath having a closed end defining a respective one of said walls and being in sealed relation about said needle.

9. The combination as set forth in claim 8 wherein said hub has a conically shaped bore and said holder is matingly received in said bore.

10. The combination as set forth in claim 8 wherein each sheath is made of rubber.

11. The combination as set forth in claim 10 wherein each said wall has a thickness of from 0.010 to 0.040 inches.

12. In combination
    a catheter assembly having a hub, a catheter needle secured to and extending from said hub to define a flow path and a tube secured to and within said hub coaxially of said catheter;
    a male luer connector having a longitudinal bore slidably received one end of said tube therein in seal-tight relation and a forward end matingly received in said hub; and
    a pair of elastomeric sheaths mounted on said one end of said tube and being compressed between said forward end of said male luer connector and an interior of said hub, said sheaths being expandable into a position sealing over said one end of said tube upon removal of said male luer connector from said catheter assembly to seal said tube against a flow of blood from said catheter.

13. The combination as set forth in claim 12 wherein each sheath is made of rubber.

14. The combination as set forth in claim 13 wherein each sheath is of a thickness in the range of from 0.010 to 0.040 inches.

* * * * *

UNITED STATES PATENT AND TRADEMARK OFFICE
CERTIFICATE OF CORRECTION

PATENT NO. : 5,234,410
DATED : Aug. 10, 1993
INVENTOR(S) : Chad D. Graham, Rex. R. Weeks It is certified that error appears in the above-identified patent and that said Letters Patent is hereby corrected as shown below:

Column 1, lines 58 to 59, cancel "needle"
Column 3, line 4, after "accordance" insert --with the--
   Line 7, after "invention" insert --and
Column 6, line 37, cancel "needle"

Signed and Sealed this

Third Day of May, 1994

Attest:

BRUCE LEHMAN

Attesting Officer

Commissioner of Patents and Trademarks